(12) United States Patent
Abe

(10) Patent No.: US 9,730,588 B2
(45) Date of Patent: Aug. 15, 2017

(54) PHOTOACOUSTIC MEASUREMENT DEVICE AND PROBE FOR PHOTOACOUSTIC MEASUREMENT DEVICE

(71) Applicant: FUJIFILM Corporation, Tokyo (JP)

(72) Inventor: Takeya Abe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 515 days.

(21) Appl. No.: 14/519,809

(22) Filed: Oct. 21, 2014

(65) Prior Publication Data

US 2015/0038825 A1 Feb. 5, 2015

Related U.S. Application Data

(63) Continuation of application No. PCT/JP2013/061494, filed on Apr. 18, 2013.

(30) Foreign Application Priority Data

May 8, 2012 (JP) .................................. 2012-106431

(51) Int. Cl.
*A61B 8/00* (2006.01)
*A61B 5/00* (2006.01)
(Continued)

(52) U.S. Cl.
CPC .......... *A61B 5/0095* (2013.01); *A61B 5/0035* (2013.01); *A61B 8/4416* (2013.01);
(Continued)

(58) Field of Classification Search
CPC ... A61B 5/0095; A61B 5/0035; A61B 8/4416; A61B 8/4444; A61B 8/14; A61B 8/463;
(Continued)

(56) References Cited

U.S. PATENT DOCUMENTS 6,426,990 B1\* 7/2002 Cesmeli ................. A61B 6/504
378/4
7,525,661 B2\* 4/2009 Mandelis ............. G01B 21/085
356/237.1
(Continued)

FOREIGN PATENT DOCUMENTS

JP 2005-21380 A 1/2005
JP 2009-31268 A 2/2009

OTHER PUBLICATIONS

International Search Report, mailed Jul. 9, 2013, issued in PCT/JP2013/061494.
(Continued)

*Primary Examiner* — Sanjay Cattungal
(74) *Attorney, Agent, or Firm* — Birch, Stewart, Kolasch & Birch, LLP

(57) ABSTRACT

An object of the invention is to reduce the size of a probe for a photoacoustic measurement device. A light guide 71 is arranged such that one of a two side surfaces 71a is closer to a probe axis C which faces a subject than the other side surface and a light emission end surface 71c is closer to the probe axis C than a light incident end surface 71b when the probe is used. When a refractive index of the light guide 71 with respect to the light is n1 and a refractive index of a medium around the light guide with respect to the light during photoacoustic measurement is n2 (n2<n1), the light emission end surface 71c is obliquely formed such that an angle α[°] (where 90°−arcsin(n2/n1)<α<90°) is formed between the light emission end surface 71c and the side surface 71a.

20 Claims, 24 Drawing Sheets

(51) Int. Cl.
*G01N 29/24* (2006.01)
*A61B 8/14* (2006.01)
*A61B 8/08* (2006.01)

(52) U.S. Cl.
CPC ....... *A61B 8/4444* (2013.01); *G01N 29/2418* (2013.01); *G01N 29/2462* (2013.01); *A61B 8/14* (2013.01); *A61B 8/463* (2013.01); *A61B 8/5246* (2013.01); *G01N 2291/023* (2013.01)

(58) Field of Classification Search
CPC ............. A61B 8/5246; G01N 29/2418; G01N 29/2462; G01N 2291/023
USPC .................................................. 600/437–480
See application file for complete search history.

(56) References Cited

U.S. PATENT DOCUMENTS

| | | | | |
|---|---|---|---|---|
| 8,144,327 B2 * | 3/2012 | Nakajima | ............ | A61B 5/0059 356/432 |
| 2003/0002616 A1 * | 1/2003 | Cesmeli | ................ | A61B 6/541 378/8 |
| 2003/0028098 A1 * | 2/2003 | Brock-Fisher | ......... | A61B 8/481 600/431 |
| 2005/0004458 A1 | 1/2005 | Kanayama et al. | | |
| 2005/0175143 A1 * | 8/2005 | Miyazaki | ............... | A61B 6/032 378/19 |
| 2006/0235302 A1 * | 10/2006 | Grossman | ................ | A61B 8/08 600/443 |
| 2007/0083109 A1 * | 4/2007 | Ustuner | .............. | G01S 7/52046 600/437 |
| 2007/0129627 A1 * | 6/2007 | Profio | .................... | A61B 6/032 600/407 |
| 2007/0232886 A1 * | 10/2007 | Camus | ..................... | A61B 6/12 600/407 |
| 2008/0273778 A1 * | 11/2008 | Goto | ..................... | G06T 11/006 382/131 |
| 2008/0285048 A1 * | 11/2008 | Chen | .................. | G01B 11/2441 356/492 |
| 2008/0294150 A1 * | 11/2008 | Altshuler | .............. | A61B 18/203 606/3 |
| 2008/0306471 A1 * | 12/2008 | Altshuler | ............... | A61B 5/441 606/10 |
| 2009/0309895 A1 * | 12/2009 | Nagase | ................ | G09G 3/2022 345/589 |
| 2011/0125017 A1 * | 5/2011 | Ramamurthy | ........... | A61B 8/08 600/443 |

OTHER PUBLICATIONS

Written Opinion of the International Searching Authority, mailed Jul. 9, 2013, issued in PCT/JP2013/061494.
X. Wang et al., "A High-Speed Photoacoustic Tomography System based on a Commercial Ultrasound and a Custom Transducer Array", Proc. of SPIE vol. 7564, pp. 756424-1-756424-9, Feb. 23, 2010.

* cited by examiner

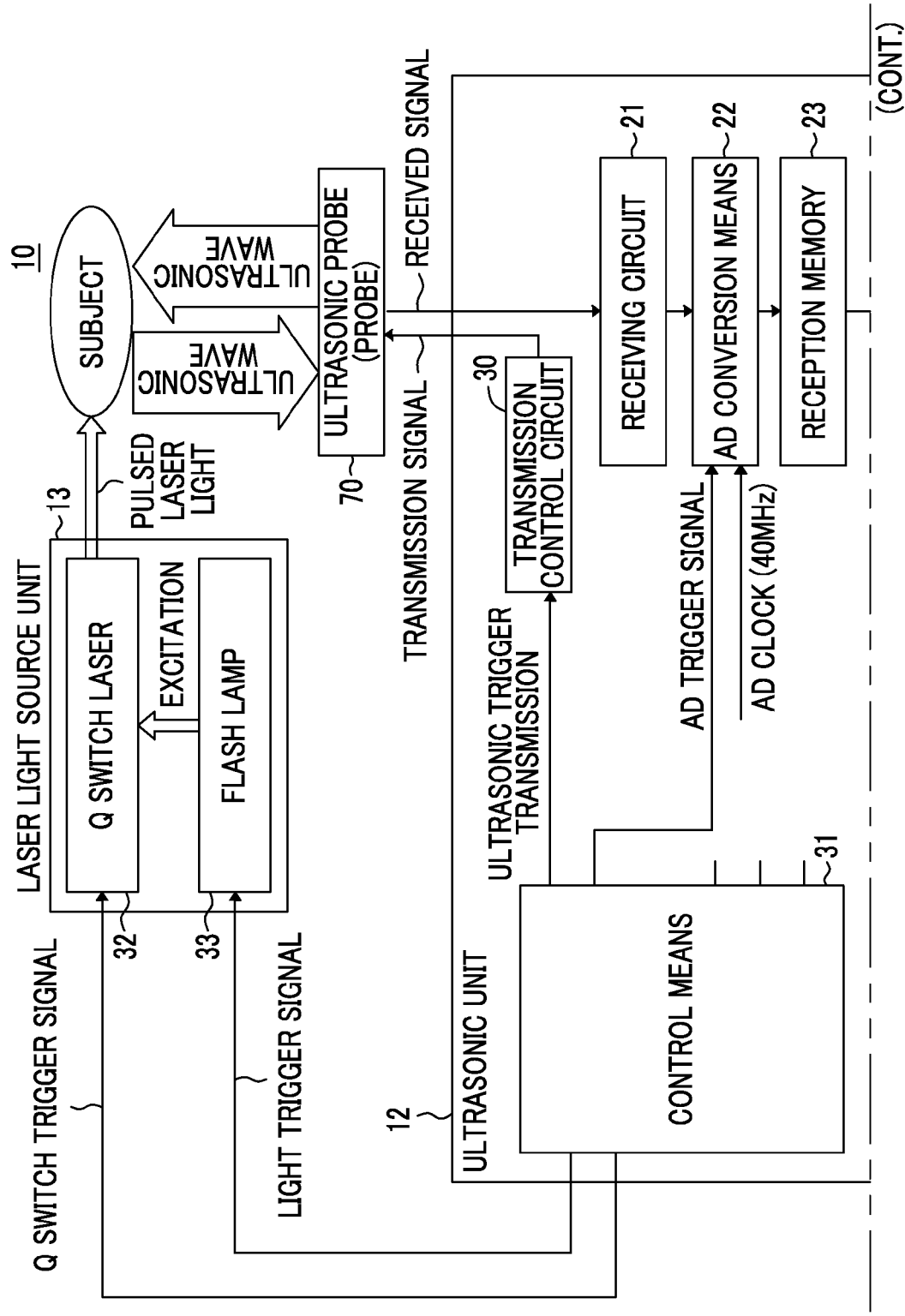

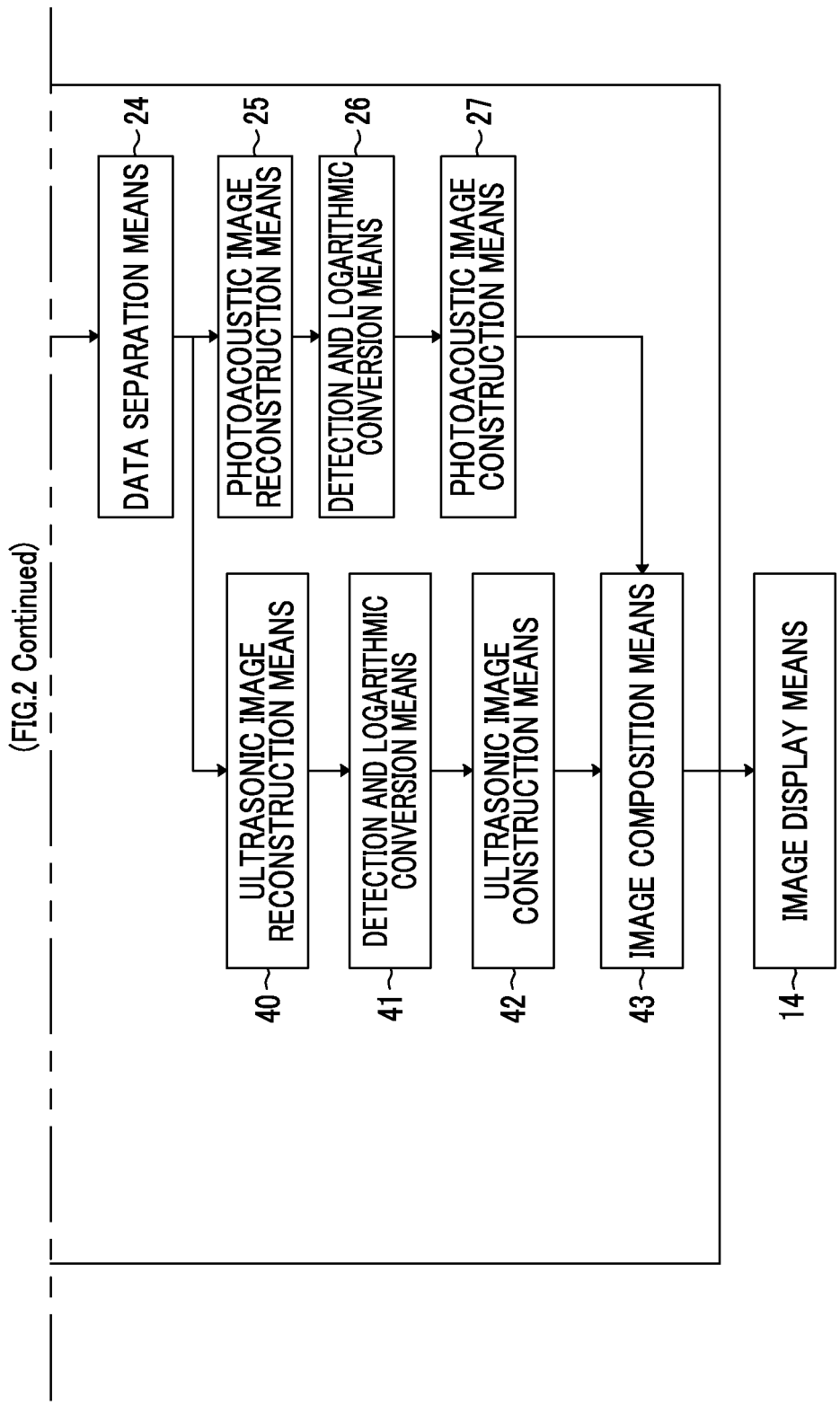

PHOTOACOUSTIC MEASUREMENT DEVICE AND PROBE FOR PHOTOACOUSTIC MEASUREMENT DEVICE

CROSS-REFERENCE TO RELATED APPLICATIONS

This application is a Continuation of PCT International Application No. PCT/JP2013/061494 filed on Apr. 18, 2013, which claims priority under 35 U.S.C §119(a) to Japanese Patent Application No. 2012-106431 filed on May 8, 2012. Each of the above applications is hereby expressly incorporated by reference, in its entirety, into the present application.

BACKGROUND OF THE INVENTION

1. Field of the Invention

The present invention relates to a photoacoustic measurement device, that is, a device that radiates light to a subject, such as a body tissue, detects an acoustic wave generated by the light irradiation, and performs measurement related to the subject.

In addition, the invention relates to a probe used for the photoacoustic measurement device.

2. Description of the Related Art

Photoacoustic imaging devices have been known which image the inside of a living body using a photoacoustic effect, as disclosed in, for example, JP2005-21380A and JP2009-31268A or "A High-Speed Photoacoustic Tomography System based on a Commercial Ultrasound and a Custom Transducer Array," Xueding Wang, Jonathan Cannata, Derek DeBusschere, Changhong Hu, J. Brian Fowlkes, and Paul Carson, Proc. SPIE Vol. 7564, 756424 (Feb. 23, 2010). In the photoacoustic imaging device, for example, pulsed light, such as pulsed laser light, is radiated into the living body. In the living body irradiated with the pulsed light, the body tissue absorbs the energy of the pulsed light, the volume of the body tissue is increased by heat, and the body tissue generates acoustic waves. Then, the acoustic waves are detected by, for example, an ultrasonic probe and the inside of the living body is visualized on the basis of an electric signal (photoacoustic signal) obtained from the acoustic waves.

In many cases, the probe which is used for the photoacoustic measurement device, such as the photoacoustic imaging device, also has a function of emitting light to be radiated to the subject. In this case, it is desirable to radiate the flux of light with uniform intensity to the part to be imaged in the subject. For example, as described in JP2009-31268A, it is considered that light is incident on a light guide and the flux of light emitted from the light guide is radiated to the subject.

The light guide is configured such that the total reflection of light is repeated therein and the intensity distribution of irradiation light is uniform. In general, the light guide has a parallel plate shape and includes two side surfaces which are parallel to each other, a light incident end surface on which light is incident, and a light emission end surface which is opposite to the light incident end surface, with the side surfaces interposed therebetween, and from which light is emitted.

SUMMARY OF THE INVENTION

However, in the above-mentioned probe, generally, an acoustic wave detection unit, such as an ultrasonic oscillator which detects the acoustic waves emitted from, for example, the inside of the living body, is arranged on a probe axis. Therefore, it is considered that the light guide having a parallel plate shape is obliquely arranged with respect to the probe axis so as not to interfere with the acoustic wave detection unit. As such, when the light guide is obliquely arranged, the amount of light which is absorbed in the vicinity of the surface of the subject is reduced and light can reach a deep position, as compared to a case in which the light guide is vertically arranged (that is, an arrangement state in which the light guide is parallel to the probe axis and vertically faces the surface of the subject).

However, when the light guide is obliquely arranged, the width of the probe is greater than that when the light guide is vertically arranged.

The invention has been made in view of the above-mentioned problems and an object of the invention is to provide a probe for a photoacoustic measurement device which has a small width and a small size even though a light guide is obliquely arranged.

Another object of the invention is to provide a photoacoustic measurement device that includes the probe and has a small size.

According to an aspect of the invention, a probe for a photoacoustic measurement device includes a light irradiation unit that emits light to be radiated to a subject and an acoustic wave detection unit that detects an acoustic wave which is emitted from the subject by the light irradiation. The light irradiation unit includes a light guide that has a parallel plate shape and includes two side surfaces which are parallel to each other, a light incident end surface on which the light is incident, and a light emission end surface which is opposite to the light incident end surface, with the side surfaces interposed therebetween, and from which the light is emitted. The light guide is arranged such that one of the two side surfaces is closer to a probe axis which faces the subject than the other side surface and the light emission end surface is closer to the probe axis than the light incident end surface when the probe is used. When a refractive index of the light guide with respect to the light is n1 and a refractive index of a medium around the light guide with respect to the light during photoacoustic measurement is n2 (n2<n1), the light emission end surface is formed such that an angle α[°] (where 90°−arcsin(n2/n1)<α<90°) is formed between the light emission end surface and the side surface which is closer to the probe axis.

In the probe for a photoacoustic measurement device according to the invention having the above-mentioned structure, when an incident angle of light, which travels in parallel to the two side surfaces in the light guide and is emitted from the light emission end surface, with respect to a plane perpendicular to the probe axis is β1 and an inclination angle of the light guide with respect to the probe axis is β2, the following expression is satisfied:

$$\frac{\sin(90° - \alpha)}{\sin(90° - \alpha + \beta 1 - \beta 2)} = \frac{n2}{n1} \quad \text{[Expression 1]}$$

In the probe for a photoacoustic measurement device according to the invention, preferably, an arrangement angle of the light guide is changeable.

In this case, preferably, the arrangement angle of the light guide is changeable between a predetermined angle with respect to the probe axis and an angle which is parallel to the probe axis.

In the probe for a photoacoustic measurement device according to the invention, in particular, when a plurality of the acoustic wave detection units are arranged in a line in a direction perpendicular to the probe axis, the light guide is preferably arranged such that the light emission end surface extends in the arrangement direction of the plurality of acoustic wave detection units.

In the probe for a photoacoustic measurement device according to the invention, preferably, two light guides are provided, with the probe axis interposed therebetween.

Preferably, the probe for a photoacoustic measurement device according to the invention further includes shutters that are provided so as to correspond to the two light guides and control light transmission such that light which passes through the light guides is radiated to the subject for different periods.

Preferably, the probe for a photoacoustic measurement device according to the invention further includes optical fibers through which light emitted from a light source is propagated. Preferably, the optical fibers are optically coupled to the light incident end surface of the light guide.

In this case, preferably, when three or more optical fibers are provided, they are arranged in a zigzag pattern in the light incident end surface of the light guide and are coupled to the light incident end surface.

When the optical fibers are provided, preferably, a light absorber adheres to a portion of the light incident end surface of the light guide in which the optical fiber is not arranged.

Preferably, the probe for a photoacoustic measurement device according to the invention further includes an optical sensor that detects light which is emitted from the light incident end surface of the light guide to the outside of the light guide.

Preferably, the probe for a photoacoustic measurement device according to the invention further includes a contact sensor that detects a contact of the probe with the subject.

In the probe for a photoacoustic measurement device according to the invention, preferably, the angle $\alpha$ is in a range of $90°-\arcsin(1.33/n1)<\alpha<90°$.

According to another aspect of the invention, a photoacoustic measurement device includes the probe for a photoacoustic measurement device according to the invention.

According to the probe for a photoacoustic measurement device of the invention, when the refractive index of the light guide with respect to the light radiated to the subject is n1 and the refractive index of the medium around the light guide with respect to the light during photoacoustic measurement is n2 (n2<n1), the light emission end surface is obliquely formed such that the angle $\alpha[°]$ (where $90°-\arcsin(n2/n1)<\alpha<90°$) is formed between the light emission end surface and the side surface which is closer to the probe axis. Therefore, when light is radiated to the subject at a common angle, the inclination angle of the light guide can be reduced, that is, the light guide can be arranged in a direction close to the vertical direction, as compared to a case in which the light emission end surface is not obliquely formed. Therefore, the width of the probe for a photoacoustic measurement device can be reduced and the size thereof can be reduced.

In the probe for a photoacoustic measurement device according to the invention, in particular, when the above-mentioned (Expression 1) is satisfied, the direction of the flux of light emitted from the light guide can be controlled such that a substantially central portion of the flux of light is incident on the plane perpendicular to the probe axis at a desired incident angle $\beta1$. The detailed reason will be described in the following embodiment.

In the probe for a photoacoustic measurement device according to the invention, in particular, when the arrangement angle of the light guide is changeable, the direction of the flux of light emitted from the light guide can be appropriately set, depending on the depth of a part of the subject that is desired to be measured (for example, a part which is desired to be imaged in the imaging device). For example, specifically, when the arrangement angle of the light guide is changeable between a predetermined angle formed with respect to the probe axis and an angle parallel to the probe axis, the arrangement angle is set to the former angle to measure a deep part of the subject and is set to the latter angle to measure a shallow part of the subject.

In the probe for a photoacoustic measurement device according to the invention, in particular, when two light guides are provided with the probe axis interposed therebetween, it is possible to irradiate the subject with a large amount of light using the light guides.

In this case, particularly, when the shutters that correspond to the two light guides and control light transmission such that light which passes through the light guides is radiated to the subject for different periods are provided, it is possible to obtain a measurement signal with a high S/N ratio. The detailed reason will be described in the embodiment applied to the photoacoustic imaging device.

In the probe for a photoacoustic measurement device according to the invention, particularly, when three or more optical fibers through which light emitted from the light source is propagated are provided in a zigzag pattern in the light incident end surface of the light guide and are coupled to the light incident end surface, it is possible to noticeably improve the uniformization effect of light intensity by the light guide.

When the optical fibers are provided, particularly, the light absorber adheres to a portion of the light incident end surface of the light guide in which the optical fiber is not arranged. In this case, it is possible to prevent the leakage of light from the light incident end surface.

In the probe for a photoacoustic measurement device according to the invention, particularly, the optical sensor that detects light emitted from the light incident end surface of the light guide to the outside of the light guide is provided. In this case, when the optical sensor detects leakage light, it is possible to prevent the adverse effect of the leakage light by, for example, reducing the output of the light source.

In the probe for a photoacoustic measurement device according to the invention, particularly, the contact sensor that detects the contact of the probe with the subject is provided. In this case, only when the contact is detected, the light source emits light with a predetermined intensity. Therefore, it is possible to prevent light with high intensity from being unnecessarily radiated from the probe.

In the probe for a photoacoustic measurement device according to the invention, particularly, the angle $\alpha$ is in the range of $90°-\arcsin(1.33/n1)<\alpha<90°$. In this case, when the subject is a living body, the above-mentioned various effects are obtained. That is, when the subject is a living body, the refractive index n2 of the living body, which is a medium around the light guide, is basically equal to the refractive index of water. In this case, generally, light with a wavelength of about 750 nm to 800 nm is radiated to the living body. The refractive index of water with respect to the wavelength is appropriately 1.33 (for example, 1.328 with respect to a wavelength of 780 nm at 20° C.). Therefore, when the angle $\alpha$ is in the above-mentioned range in which n2 is 1.33 and the subject is a living body, the above-mentioned various effects are obtained.

In addition, the photoacoustic measurement device according to the invention includes the probe for a photoacoustic measurement device according to the invention. Therefore, it is possible to reduce the size of a portion of the photoacoustic measurement device around the probe.

BRIEF DESCRIPTION OF THE DRAWINGS

FIG. 2 is a block diagram illustrating the schematic structure of a photoacoustic imaging device including the probe shown in FIG. 1.

DESCRIPTION OF THE PREFERRED EMBODIMENTS

Figure 1:
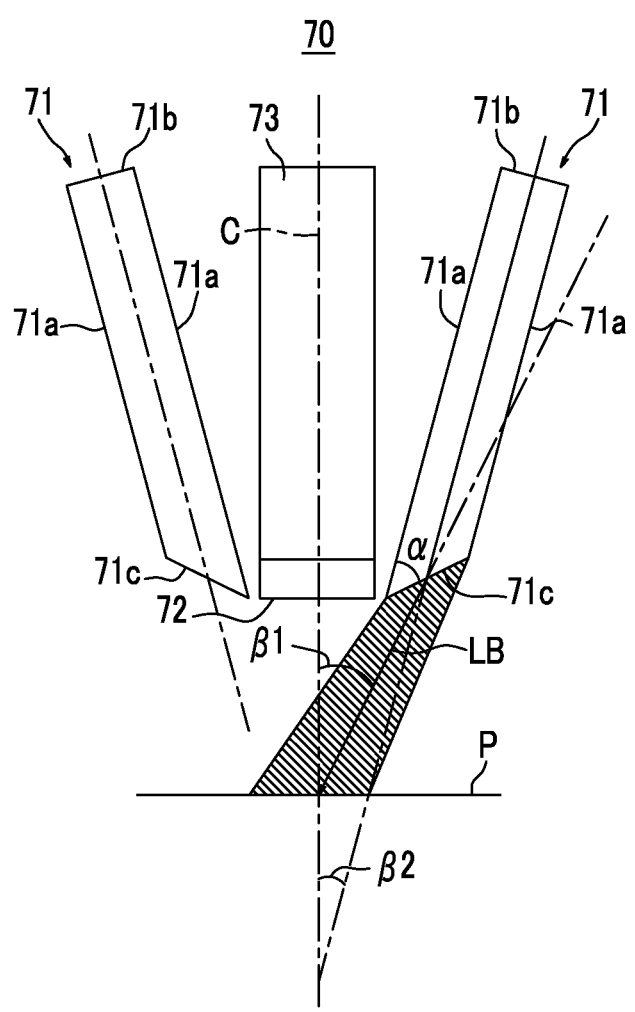
FIG. 1 is a schematic side view illustrating a main portion of a probe for a photoacoustic measurement device according to an embodiment of the invention.

Hereinafter, embodiments of the invention will be described in detail with reference to the drawings. FIG. 1 shows the schematic shape of a side surface of a main portion of an ultrasonic probe (hereinafter, simply referred to as a probe) 70 according to an embodiment of the invention. FIG. 2 shows a photoacoustic imaging device 10 as an example of a photoacoustic measurement device to which the probe 70 is applied.

First, the photoacoustic imaging device 10 will be described with reference to FIG. 2. The photoacoustic imaging device 10 can acquire, for example, both photoacoustic images and ultrasonic images and includes an ultrasonic unit 12, a laser light source unit 13, and image display means 14, in addition to the probe 70.

The laser light source unit 13 emits pulsed laser light with a predetermined wavelength and the pulsed laser light emitted from the laser light source unit 13 is radiated to a subject. The emission path of the pulsed laser light is schematically shown in FIG. 1. For example, the pulsed laser light is guided to the probe 70 by light guide means, such as a plurality of optical fibers, is propagated through a light guide (light guide plate) which is provided in the probe 70, and is radiated from the light guide to the subject, which will be described in detail below.

The probe 70 outputs (transmits) ultrasonic waves to the subject and detects (receives) ultrasonic waves reflected from the subject. In order to output and detect the ultrasonic waves, the probe 70 includes, for example, a plurality of ultrasonic oscillators (ultrasonic transducers) which are one-dimensionally arranged. In addition, the probe 70 detects ultrasonic waves (acoustic waves), which are generated by the absorption of laser light from the laser light source unit 13 by an observation object in the subject, using the plurality of ultrasonic oscillators. The probe 70 detects the acoustic waves and outputs an acoustic wave detection signal. In addition, the probe 70 detects the reflected ultrasonic waves and outputs an ultrasonic wave detection signal.

The light guide provided in the probe 70 will be described below. The light guide is formed in a parallel plate shape. A light emission end surface of the light guide is arranged along a direction (the left-right direction of FIG. 9) in which the plurality of ultrasonic oscillators are arranged and laser light is radiated from the light emission end surface to the subject. Next, an application example of this structure will be described.

When the photoacoustic image or ultrasonic image of the subject is acquired, the probe 70 is moved in a direction that is almost perpendicular to the one-dimensional direction in which the plurality of ultrasonic oscillators are arranged. Then, the subject is two-dimensionally scanned by laser light and ultrasonic waves. The examiner may manually move the probe 70 to perform the scanning operation or a scanning mechanism may be used to achieve precise two-dimensional scanning.

The ultrasonic unit 12 includes a receiving circuit 21, AD conversion means 22, a reception memory 23, data separation means 24, photoacoustic image reconstruction means 25, detection and logarithmic conversion means 26, and photoacoustic image construction means 27.

The receiving circuit 21 receives the acoustic wave detection signal and the ultrasonic wave detection signal output from the probe 70. The AD conversion means 22 is sampling means, samples the acoustic wave detection signal and the ultrasonic wave detection signal received by the receiving circuit 21, and converts the acoustic wave detection signal and the ultrasonic wave detection signal into photoacoustic data and ultrasonic data which are digital signals, respectively. For example, the sampling is performed in a predetermined sampling cycle in synchronization with an AD clock signal which is input from the outside.

The ultrasonic unit 12 includes ultrasonic image reconstruction means 40 that receives the output of the data separation means 24, detection and logarithmic conversion means 41, ultrasonic image construction means 42, and image composition means 43 that receives the outputs of the ultrasonic image construction means 42 and the photoacoustic image construction means 27. The output of the image composition means 43 is input to the image display means 14 such as a CRT or a liquid crystal display device. In addition, the ultrasonic unit 12 includes a transmission control circuit 30 and control means 31 for controlling the operation of each component in the ultrasonic unit 12.

The photoacoustic data or ultrasonic data output from the AD conversion means 22 is temporarily stored in the reception memory and is then input to the data separation means 24. The data separation means 24 separates the input photoacoustic data and ultrasonic data, inputs the photoacoustic data to the photoacoustic image reconstruction means 25, and inputs the ultrasonic data to the ultrasonic image reconstruction means 40.

The laser light source unit 13 is a solid-state laser unit including a Q switch pulse laser 32 which is, for example, a Nd:YAG laser, a Ti: Sapphire laser, or an alexandrite laser and a flash lamp 33 which is an excitation light source for the Q switch pulse laser 32. For example, when a photoacoustic image indicating a blood vessel is acquired, a laser light source unit that emits pulsed laser light with a wavelength which is absorbed well in the blood vessel is used as the laser light source unit 13.

When receiving a light trigger signal for instructing the emission of light from the control means 31, the laser light source unit 13 turns on the flash lamp 33 to excite the Q switch pulse laser 32. For example, when the flash lamp 33 sufficiently excites the Q switch pulse laser 32, the control means 31 outputs a Q switch trigger signal. When receiving the Q switch trigger signal, the Q switch pulse laser 32 turns on its Q switch and emits pulsed laser light.

Here, the time required until the Q switch pulse laser 32 is sufficiently excited after the flash lamp 33 is turned on can be estimated from, for example, the characteristics of the Q switch pulse laser 32. Instead of controlling the Q switch using the control means 31 as described above, the Q switch may be turned on in the laser light source unit 13 after the Q switch pulse laser 32 is sufficiently excited. In this case, a signal indicating that the Q switch has been turned on may be notified to the ultrasonic unit 12.

The control means 31 inputs an ultrasonic trigger signal for instructing the transmission of ultrasonic waves to the transmission control circuit 30. When receiving the ultrasonic trigger signal, the transmission control circuit 30 instructs the probe 70 to transmit ultrasonic waves. The control means 31 outputs the light trigger signal and then outputs the ultrasonic trigger signal. When the light trigger signal is output, laser light is radiated to the subject and acoustic waves are detected. Then, when the ultrasonic trigger signal is output, ultrasonic waves are transmitted to the subject and the reflected ultrasonic waves are detected.

In addition, the control means 31 outputs a sampling trigger signal for instructing the start of sampling to the AD conversion means 22. The sampling trigger signal is output after the light trigger signal is output and before the ultrasonic trigger signal is output, preferably, at the time when laser light is actually radiated to the subject. Therefore, the sampling trigger signal is output in synchronization with, for example, the time when the control means 31 outputs the Q switch trigger signal. When receiving the sampling trigger signal, the AD conversion means 22 starts to sample the acoustic wave detection signal which has been output from the probe 70 and then received by the receiving circuit 21.

After outputting the light trigger signal, the control means 31 outputs the ultrasonic trigger signal at the time when the detection of the acoustic waves ends. In this case, the AD conversion means 22 continuously performs the sampling, without interrupting the sampling of the acoustic wave detection signal. In other words, the control means 31 outputs the ultrasonic trigger signal in a state in which the AD conversion means 22 continuously samples the acoustic wave detection signal. The probe 70 transmits ultrasonic waves in response to the ultrasonic trigger signal and the object to be detected by the probe 70 is changed from acoustic waves to reflected ultrasonic waves. The AD conversion means 22 continues to sample the detected ultrasonic wave detection signal to continuously sample the acoustic wave detection signal and the ultrasonic wave detection signal.

The AD conversion means 22 stores the photoacoustic data and the ultrasonic data obtained by sampling in the common reception memory 23. The sampling data stored in the reception memory 23 is photoacoustic data at a certain point of time and is ultrasonic data at another certain point of time. The data separation means 24 separates the photoacoustic data and the ultrasonic data stored in the reception memory 23, inputs the photoacoustic data to the photoacoustic image reconstruction means 25, and inputs the ultrasonic data to the ultrasonic image reconstruction means 40.

Next, the generation and display of the ultrasonic image and the photoacoustic image will be described. The ultrasonic image reconstruction means 40 adds the ultrasonic data which is data for each of the plurality of ultrasonic oscillators of the probe 70 to generate ultrasonic tomographic image data corresponding to one line. The detection and logarithmic conversion means 41 generates an envelope of the ultrasonic tomographic image data, performs logarithmic conversion on the envelope to widen a dynamic range, and inputs the data to the ultrasonic image construction means 42. The ultrasonic image construction means 42 generates an ultrasonic tomographic image (ultrasonic echo image) on the basis of the data of each line output from the detection and logarithmic conversion means 41. That is, the ultrasonic image construction means 42 converts, for example, the position of the peak of the ultrasonic wave detection signal in the time axis direction into a position in the depth direction of a tomographic image to generate the ultrasonic tomographic image.

The above-mentioned process is sequentially performed with the scanning and movement of the probe 70 to generate the ultrasonic tomographic images of a plurality of parts of the subject in the scanning direction. Then, image data which carries the ultrasonic tomographic images is input to the image composition means 43. When only the ultrasonic tomographic image is desired to be displayed, the image data which carries the ultrasonic tomographic images is transmitted to the image display means 14, without passing through the image composition means 43. The ultrasonic tomographic image is displayed on the image display means 14.

Next, the generation and display of the photoacoustic image will be described. The photoacoustic data which is separated from the ultrasonic data in the data separation means 24, for example, photoacoustic data obtained by irradiating the subject with pulsed laser light with a wavelength which is absorbed by the blood vessel is input to the photoacoustic image reconstruction means 25. The photoacoustic image reconstruction means 25 adds the photoacoustic data which is data for each of the plurality of ultrasonic oscillators of the probe 70 to generate photoacoustic image data corresponding to one line. The detection and logarithmic conversion means 26 generates an envelope of the photoacoustic image data, performs logarithmic conversion on the envelope to widen a dynamic range, and inputs the data to the photoacoustic image construction means 27. The photoacoustic image construction means 27 generates a photoacoustic image on the basis of photoacoustic image data for each line. That is, the photoacoustic image construction means 27 converts, for example, the position of the peak of the photoacoustic image data in the time axis direction into a position in the depth direction of a tomographic image to generate the photoacoustic image.

The above-mentioned process is sequentially performed with the scanning and movement of the probe 70 to generate the photoacoustic images of a plurality of parts of the subject in the scanning direction. Then, image data which carries the photoacoustic images is input to the image composition means 43 and is composed with the image data which carries the ultrasonic tomographic images. The image carried by the composite data is displayed on the image display means 14. In the image which is displayed on the basis of the composite data, a blood vessel image which is the photoacoustic image is displayed in the ultrasonic tomographic image. The blood vessel image may have a predetermined color so as to be clearly distinguished from other parts.

Next, the probe 70 will be described in detail with reference to FIG. 1. As shown in FIG. 1, the probe 70 includes two light guides 71 forming a light irradiation unit that emits laser light to the subject and a plurality of ultrasonic oscillators 72 functioning as an acoustic wave detection unit that detects the acoustic waves emitted from the subject irradiated with the laser light. As described above, the ultrasonic oscillators 72 generate ultrasonic waves in order to acquire an ultrasonic image echo and detect the ultrasonic waves reflected from the subject.

The plurality of ultrasonic oscillators 72 are arranged in a line in a direction perpendicular to the plane of paper in FIG. 1 (which is the left-right direction in FIG. 9 and is referred to as a detection unit arrangement direction) and are attached to the lower end of a base portion 73 with a substantially rectangular parallelepiped shape. The detection unit arrangement direction is a direction perpendicular to a probe axis C which faces the subject when the probe is used, that is, an axis which extends from the center of the base portion 73

One the other hand, the light guide 71 has a substantially parallel plate shape and includes two side surfaces 71a which are parallel to each other, a light incident end surface 71b on which laser light is incident, and a light emission end surface 71c which is opposite to the light incident end surface 71b, with the side surfaces 71a interposed therebetween and from which the laser light is emitted. Each of the two light guides 71 is arranged such that one of the two side surfaces 71a is closer to the probe axis C than the other side surface, the light emission end surface 71c is closer to the probe axis C than the light incident end surface 71b, and the light emission end surface 71c is inclined while extending in the detection unit arrangement direction.

Here, the light emission end surface 71c of the light guide 71 is obliquely formed so as to form an angle $\alpha[°]$ with respect to the side surface 71a which is closer to the probe axis C. In this case, the angle $\alpha$ is set so as to satisfy the following relationship when the refractive index of the light guide 71 is n1 and the refractive index of a medium around the light guide is n2: $90°-\arcsin(n2/n1)<\alpha<90°$. The light guide 71 is generally made of optical glass which will be described below. The medium around the light guide is generally air or a body tissue which is considered to have the same refractive index as water. Therefore, in general, n2<n1 is satisfied.

Next, the operation when the above-mentioned relationship is satisfied will be described with reference to FIG. 3. For example, a plurality of optical fibers are optically coupled to the light incident end surface 71b of the light guide 71 and laser light is propagated through the optical fibers and is then introduced into the light guide 71. The laser light is propagated while being repeatedly and totally reflected in the light guide 71 and is emitted from the light incident end surface 71b to the subject.

When light is introduced into the light guide 71 through the optical fibers as described above, the entire light is basically obliquely incident on the light incident end surface 71b of the light guide 71. Therefore, there is little light which travels in parallel to the side surface 71a in the light guide 71. However, as shown in FIGS. 1 and 3, it is assumed that there is laser light LB which travels in parallel to the side surface 71a and conditions are determined such that the laser light LB is refracted from the light emission end surface 71c into the probe.

Figure 4:
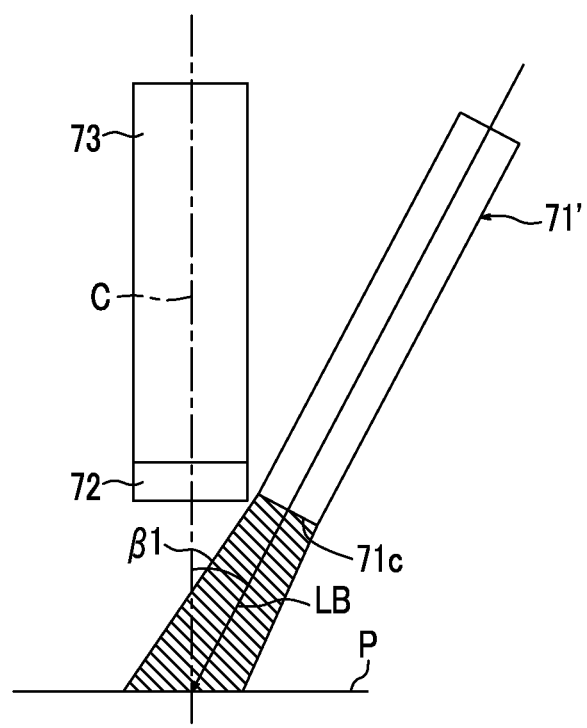
FIG. 4 is a schematic side view illustrating a portion of a probe according to the related art.

That is, under the above-mentioned conditions, the entire flux of light (which is a hatched portion in FIG. 1 and is a group of light rays that are emitted from the light emission end surface 71c at various angles) which is emitted from the light emission end surface 71c while being spread is refracted to the inside of the probe. In this case, when a predetermined region that is disposed immediately below the ultrasonic oscillator 72 is desired to be irradiated with the flux of light, the inclination angle β2 of the light guide 71 can be set to be less than that when the region is irradiated with light by a general light guide 71' having a light emission end surface 71c that is not inclined as shown in FIG. 4. In addition, it is possible to further reduce the width of the probe 70 which depends on the position of the outer end of the light guide 71.

Here, the angle $\alpha$ may be an acute angle, that is, $\alpha<90°$ is satisfied in order to refract the laser light LB that travels as described above from the light emission end surface 71c into the probe. In addition, the condition that the incident angle $\theta_A$ of the laser light LB that travels as described above with respect to the light emission end surface 71c is less than a critical angle needs to be satisfied in order to prevent the laser light LB that travels as described above from being totally reflected from an interface between the light emission end surface 71c and the medium around the light emission end surface 71c. Since the incident angle $\theta_A$ is $90°-\alpha$ and the critical angle is $\arcsin(n2/n1)$, this condition is $90°-\alpha<\arcsin(n2/n1)$, that is, $90°-\arcsin(n2/n1)<\alpha$.

As described above, when the condition $90°-\arcsin(n2/n1)<\alpha<90°$ is satisfied, a sufficient amount of light emitted from the light emission end surface 71c is ensured. Moreover, the width of the probe 70 can be less than that when a light guide having a light emission end surface which is not obliquely formed is used.

Next, conditions when the laser light LB which travels in parallel to the side surface 71a in the light guide 71 is incident on a plane P perpendicular to the probe axis C at a desired incident angle will be described with reference to FIG. 3. Here, the right light guide 71 in FIGS. 1 and 3 will be described. However, the conditions are the same as those related to the left light guide 71.

First, in this case, it is assumed that the refractive index n1 of the light guide 71 and the refractive index n2 of the medium around the light guide 71 satisfy n2<n1. In addition, it is assumed that the desired incident angle is β1 and the inclination angle of the light guide 71 with respect to the probe axis C is β2.

As described above, the laser light LB that travels in parallel to the side surface 71a in the light guide 71 is refracted at the interface between the light emission end surface 71c and the surrounding medium and is emitted from the light emission end surface 71c. In this case, when the incident angle and refraction angle of the laser light LB with respect to the interface are $\theta_A$ and $\theta_B$, respectively, the following Expression 2 is obtained from the Snell's law.

$$\frac{\sin\theta_A}{\sin\theta_B} = \frac{n2}{n1} \qquad \text{[Expression 2]}$$

Here, $\theta_A$ is 90°−α. In addition, when a difference between the incident angle $\theta_A$ and the refraction angle $\theta_B$ is $\theta_{OUT}$, $\theta_{OUT}$=β1−β2 is established and $\theta_B = \theta_A + \theta_{OUT} = (90°-\alpha)+\beta1-\beta2$ is established. When $\theta_A$ and $\theta_B$ are substituted into the above-mentioned (Expression 2), the above-mentioned (Expression 1) is obtained. That is, when (Expression 1) is satisfied, the laser light LB which has traveled in parallel to the side surface 71a in the light guide 71 and then emitted from the light emission end surface 71c is incident on the plane P perpendicular to the probe axis C at the desired incident angle β1.

As described above, when light is introduced from the optical fiber to the light guide 71, there is little light that travels in parallel to the side surface 71a in the light guide 71. However, when the above-mentioned light is assumed and the above-mentioned (Expression 1) is satisfied, the center of the flux of light (hatched portion) which is emitted from the light emission end surface 71c of the light guide 71 while being spread is incident on the plane P at the desired incident angle β1 as shown in FIG. 1.

When the light emission end surface 71c is not obliquely formed and the light guide 71 has a perfectly rectangular parallelepiped shape, the inclination angle β2 of the light guide 71 with respect to the probe axis C is set to be equal to the incident angle β1 in order to obtain the above-mentioned state, as shown in FIG. 4. When (Expression 1) is satisfied, the inclination angle β2 can be reduced by a value corresponding to refraction at the light emission end surface 71c, as compared to the above-mentioned case.

Figure 3:
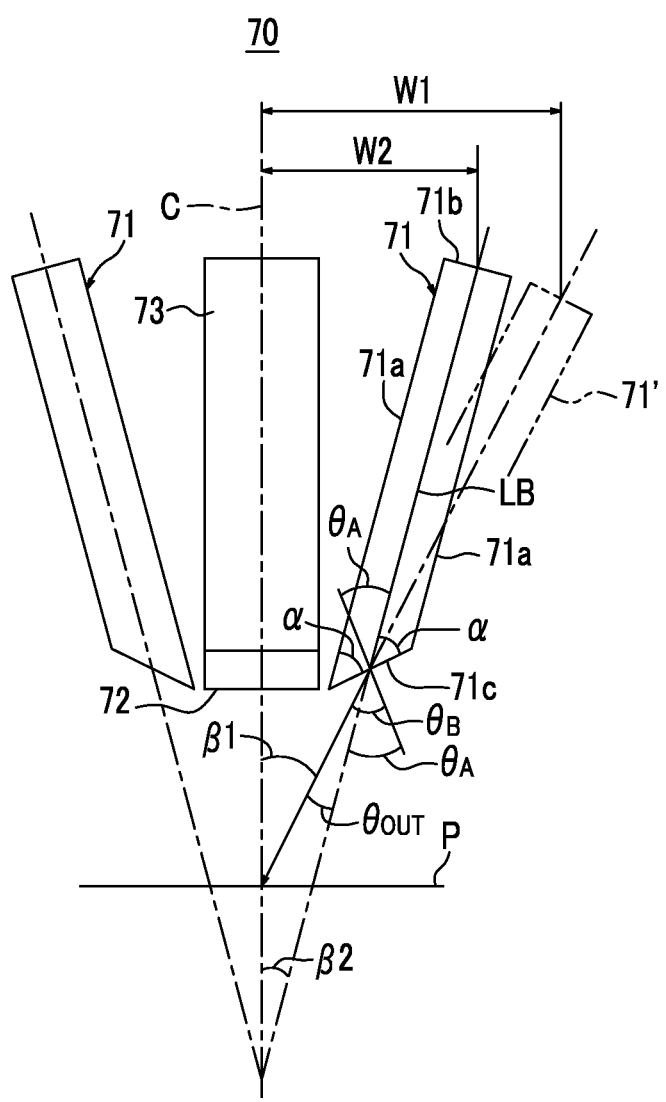
FIG. 3 is a schematic diagram illustrating the effect of the probe shown in FIG. 1.

The difference between the total width of the probe 70 when the light emission end surface 71c is obliquely formed and the total width of the probe 70 when the light emission end surface 71c is not obliquely formed is almost two times the difference between the dimensions W1 and W2 in FIG. 3. When the difference is 2ΔW and the total length of the light guide 71 (the total length of a central portion in a thickness direction) is L, 2ΔW=2 (W1−W2)=2 L(sin β1−sin β2) is established.

In the invention, the above-mentioned (Expression 1) is not necessarily satisfied. It is preferable that a part of the subject from which a photoacoustic image is desired to be acquired be basically disposed immediately below the ultrasonic oscillators 72 and the most suitable amount of light be radiated to the part. However, even when the desired incident angle β1 is obtained, a region which is irradiated with the most suitable amount of light is disposed immediately below the ultrasonic oscillators 72 or at the other positions, depending on the distance between a part of the subject and the ultrasonic oscillator 72. Conversely, even when (Expression 1) is not satisfied, the distance between a part of the subject and the ultrasonic oscillator 72 is adjusted to irradiate a desired part of the subject which is disposed immediately below the ultrasonic oscillator 72 with the most suitable amount of light.

Next, the preferred value of the angle α in the probe 70 according to this embodiment will be described. The angle α and the inclination angle β2 were set in the following four examples: an example in which the light guide 71 was made of synthetic quartz (refractive index n1=1.45); an example in which the light guide 71 was made of BK7 glass (refractive index n1=1.51); an example in which the surrounding medium was water (living body); and the surrounding medium was air. Then, a probe miniaturization effect in each example was investigated by simulation using a calculator.

Here, the value of 2ΔW is defined as a reduction in size as compared to the case in which the light emission end surface 71c is not obliquely formed, that is, a reduction in width. In this case, it is assumed that the length L of the light guide is 25 mm, the thickness thereof is 3 mm, the desired incident angle β1 is 30°, and the divergence angle of light which is emitted from the light source is defined by a $1/e^2$ diameter and is 9.2° (which is defined by the divergence angle of a portion of the flux of light that has peak intensity, that is, an intensity of $1/e^2$ with respect to the light intensity of the center of the flux of light). In this example, a sodium D line (wavelength=589.3 nm) is considered as the light used. However, other light rays may be used. In this case, the refractive indexes n1 and n2 with respect to the light used need to be considered.

The simulation results are shown in Table 1. In these cases, the angle α is set to a value at which the incident angle $\theta_A$=(90°−α) is less than the critical angle $\theta_C$ by 0.1° and a large reduction in size 2ΔW is obtained under these conditions. However, as the incident angle $\theta_A$ becomes close to the critical angle $\alpha_C$, the amount of light which is totally reflected from the interface between the light emission end surface 71c of the light guide 71 and the surrounding medium increases, which results in a reduction in irradiation efficiency.

TABLE 1

Length of Light Guide L: 25 mm
Incident angle β1: 30[°]

| Refractive index n1 of material forming light guide | Refractive index n2 of surrounding medium | Critical angle $\theta_C$[°] | Cut angle α[°] | Angle $\theta_{OUT}$[°] | Inclination angle β2[°] | 2ΔW [mm] |
|---|---|---|---|---|---|---|
| Synthetic quartz 1.45 | Water (living body) 1.33 | 66.5 | 23.6 | 22.0 | 8.0 | 18.0 |
| Synthetic quartz 1.45 | Air 1.00 | 43.6 | 46.5 | 42.0 | 0.0 | 25.0 |
| BK7 1.51 | Water (living body) 1.33 | 61.7 | 28.4 | 26.0 | 4.0 | 21.5 |
| BK7 1.51 | Air 1.00 | 41.5 | 48.6 | 46.0 | 0.0 | 25.0 |

It is preferable to increase the angle α such that the incident angle $\theta_A$ is reduced, in order to reduce the amount of totally reflected light. In the above-mentioned four examples, the angle α at which the amount of totally reflected light was 10% of the total amount of incident light was calculated by simulation. The results are shown in Table 2. As shown in Table 2, the reduction in size 2ΔW is obviously less than that in Table 1, that is, the miniaturization effect is reduced, but a sufficient amount of light radiated to the subject is ensured. Therefore, it is preferable to set the angle α to about the values shown in Table 2.

TABLE 2

Length of Light Guide L: 25 mm
Incident angle β1: 30[°]

| Refractive index n1 of material forming light guide | Refractive index n2 of surrounding medium | Critical angle $\theta_C[°]$ | Cut angle $\alpha[°]$ | Angle $\theta_{OUT}[°]$ | Inclination angle $\beta2[°]$ | 2ΔW [mm] |
|---|---|---|---|---|---|---|
| Synthetic quartz 1.45 | Water (living body) 1.33 | 66.5 | 42.5 | 6.0 | 24.0 | 4.7 |
| Synthetic quartz 1.45 | Air 1.00 | 43.6 | 66.2 | 12.0 | 18.0 | 9.5 |
| BK7 1.51 | Water (living body) 1.33 | 61.7 | 40.9 | 10.0 | 20.0 | 7.9 |
| BK7 1.51 | Air 1.00 | 41.5 | 65.9 | 14.0 | 16.0 | 11.2 |

In this embodiment, the light guide 71 has a shape in which the light emission end surface 71c is elongated along the arrangement direction of the plurality of ultrasonic oscillators 72. However, a light guide which does not have the elongated light emission end surface and is formed in a thin rod shape as a whole may be used. The invention can be similarly applied to a probe for a photoacoustic measurement device which includes the rod-shaped light guide. In this case, when a light emission end surface is obliquely inclined, it is possible to obtain the same effect as described above.

Figure 5:
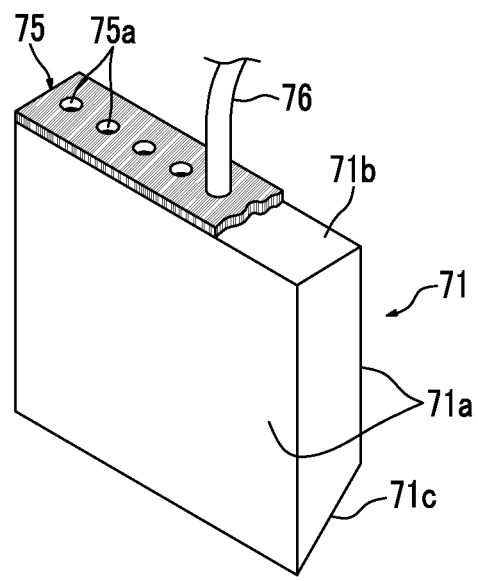
FIG. 5 is a partially cutaway perspective view illustrating a light guide of a probe according to another embodiment of the invention.

It is desirable that the light guide 71 be provided with a light absorber 75 that adheres to the light incident end surface 71b, as shown in FIG. 5. The light absorber 75 is made of a light-absorbing material, such as black rubber or carbon. When the optical fiber 76 is provided as means for guiding light, the light absorber 75 is provided with a hole 75a through which the optical fiber 76 passes. The provision of the light absorber 75 makes it possible to prevent the following: light which is totally reflected from the interface between the light emission end surface 71c and a medium around the light emission end surface 71c returns into the light guide 71 and leaks from the light incident end surface 71b, and the leakage light is unnecessarily radiated to the subject or is incident on the eyes of a probe operator. In FIG. 5, the same components as those in FIGS. 1 to 4 are denoted by the same reference numerals and the description thereof will be made only if necessary (which holds for the following).

In addition, a structure for preventing the problems caused by the leakage light will be described with reference to FIG. 6. In this structure, a probe housing 74 which accommodates the light guide 71, the base portion 73, and a part of the optical fiber 76 is provided. In the probe housing 74, an optical sensor 77 is provided at a position that faces the light incident end surface 71b of one light guide 71 and is close thereto.

The optical sensor 77 can detect the light which leaks from the light incident end surface 71b to the outside of the light guide for the above-mentioned reason. When the optical sensor 77 detects the leakage light, the output of a light source, such as the laser light source unit 13, is reduced to prevent the above-mentioned problems due to leakage light with high intensity.

Figure 6:
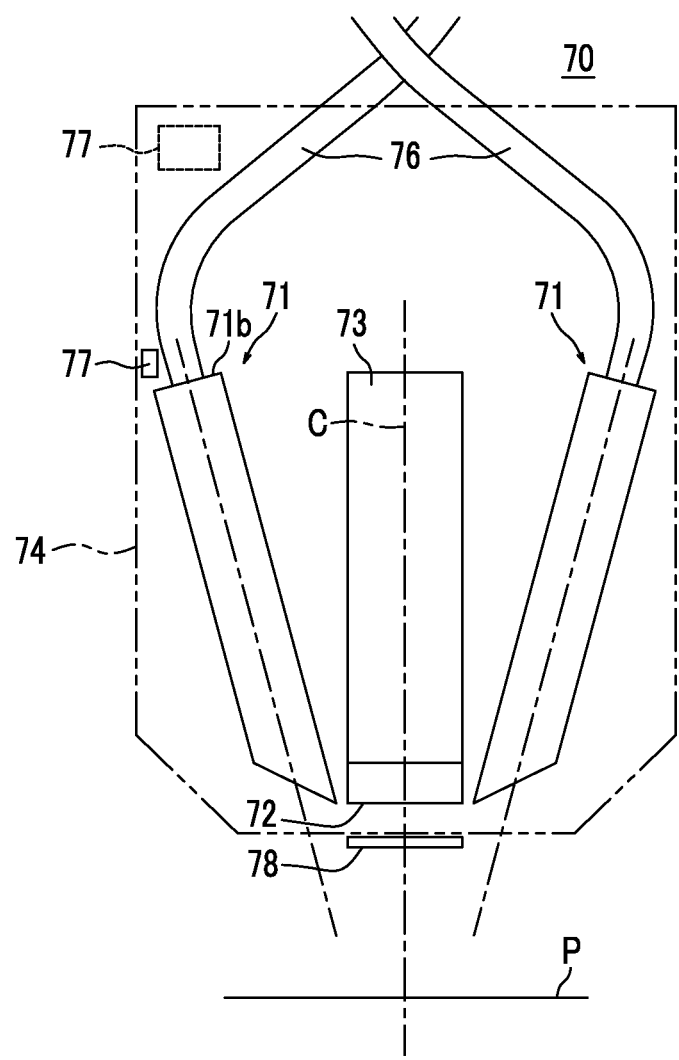
FIG. 6 is a schematic side view illustrating a portion of a probe according to still another embodiment of the invention.

When the optical sensor 77 particularly is of a large size, it may be provided at a peripheral position represented by a dashed line in FIG. 6. In this case, a space which is formed above the light guide 71 by the oblique arrangement of the light guide 71 is effectively used to provide the optical sensor.

In addition, as shown in FIG. 6, a contact sensor 78 which detects contact with the subject may be provided in the probe housing 74 and the output of a light source, such as the laser light source unit 13, may be controlled on the basis of the output of the contact sensor 78. That is, in this case, immediately after the photoacoustic imaging device 10 starts up or at the time when an operation performed before the probe is used ends, the light source outputs weak light and the output of the light source is increased to a predetermined value required for imaging only when the contact sensor 78 detects the contact of the probe with the subject during the use of the probe. In this way, it is possible to prevent high-intensity light from being unnecessarily radiated to the subject or from being incident on the eyes of the probe operator in a state in which the probe is not ready to be used.

Figure 7:
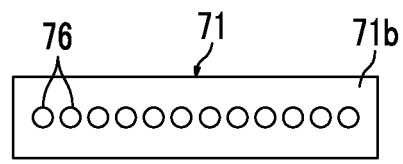
FIG. 7 is a plan view illustrating a portion of the probe according to the related art.
Figure 8:
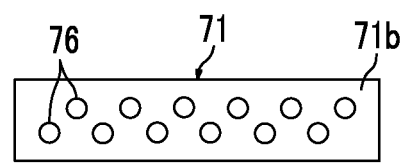
FIG. 8 is a plan view illustrating a portion of a probe according to still another embodiment of the invention.

It is desirable that the subject be irradiated with light with uniform intensity. Next, a structure for meeting the requirements will be described. FIGS. 7 and 8 show examples of the arrangement of a plurality of optical fibers 76 relative to the light incident end surface 71b of the light guide 71. As shown in FIGS. 7 and 8, the same number of optical fibers 76 is coupled to the light incident end surface 71b. In this case, in the example shown in FIG. 8 in which the optical fibers 76 are arranged in a grid shape in the vertical and horizontal directions and are arranged in a zigzag pattern as a whole (that is, of adjacent fiber rows, fibers in one fiber row are disposed between fibers in the other fiber row), light emitted from the optical fiber 76 is uniformized in the light guide 71 and is then emitted therefrom with more uniform intensity than that in the example shown in FIG. 7 in which only one row of the optical fibers 76 is arranged.

In the example shown in FIG. 8, two optical fiber rows are arranged in the thickness direction of the light guide 71 (the vertical direction of FIG. 8). However, the number of optical fiber rows is not limited to two, but three or more optical fiber rows may be provided.

Figure 9:
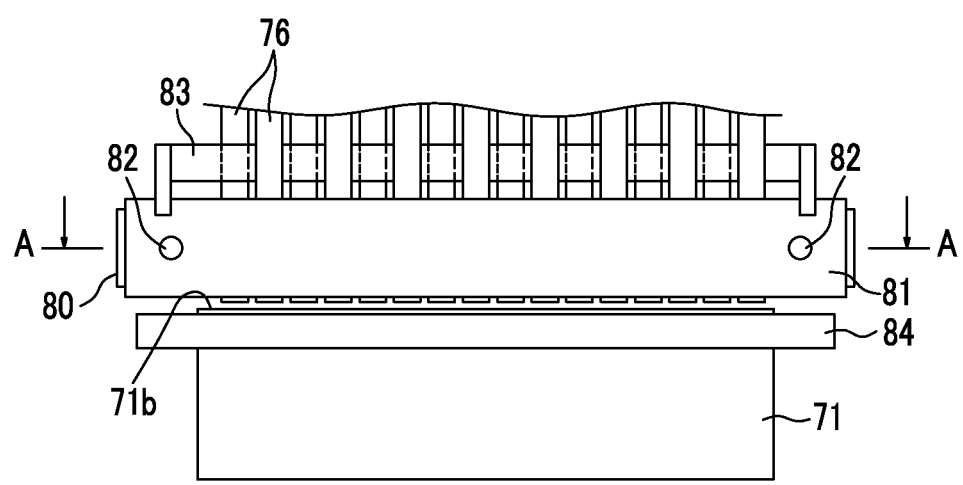
FIG. 9 is a side view illustrating another portion of the probe shown in FIG. 8.
Figure 10:
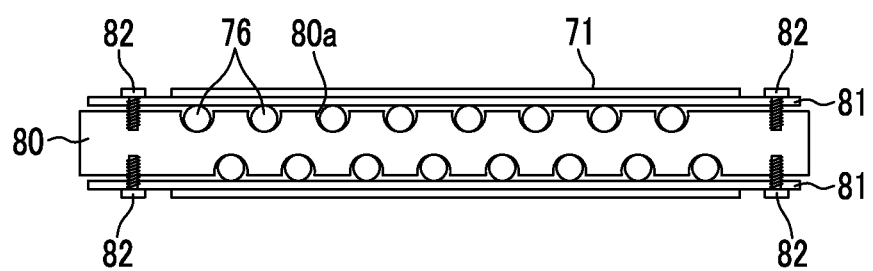
FIG. 10 is a cross-sectional view illustrating the cross-sectional shape of a portion taken along the line A-A of FIG. 9.

FIGS. 9 and 10 show a preferred fiber fixing structure when the plurality of optical fibers 76 are arranged as shown in FIG. 8. FIG. 9 shows the shape of the side surface of the structure and FIG. 10 shows the cross-sectional shape of a portion taken along the line A-A of FIG. 9. This structure includes a fiber holding member 80 in which a plurality of vertical grooves 80a for accommodating the fibers are formed in the left and right side surfaces, a pair of fiber pressing members 81 which press the lower ends of the optical fibers 76 accommodated in the vertical grooves 80a, four screws 82 which attach the fiber pressing members 81 to the fiber holding member 80, and a fiber guide member 83 which is connected to the fiber pressing member 81 and holds portions of the optical fibers 76 that are slightly higher than the lower ends. The light guide 71 is held by a light guide holding member 84, with the light incident end surface 71b, which is the upper end surface, being slightly away from the lower end surface (light emission end surface) of each optical fiber 76.

Figure 11:
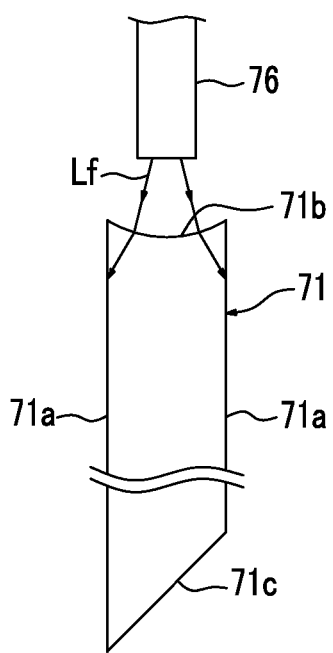
FIG. 11 is a side view illustrating a portion of a probe according to still another embodiment of the invention.

In addition, it is effective to form the light incident end surface 71b of the light guide 71 such that the cross section thereof has a concave surface shape as shown in FIG. 11 in order to irradiate the subject with light having uniform intensity. That is, when the light incident end surface 71b has the above-mentioned shape, light Lf which is incident on the light guide 71 from the optical fiber 76 is refracted to the outside of the light incident end surface 71b (to the side surface 71a) as shown in FIG. 11. Then, the number of times light is totally reflected from the interface between the side surface 71a of the light guide 71 and the surrounding medium increases. Therefore, the uniformity of the intensity distribution of light which is emitted from the light emission end surface 71c increases.

Figure 12:
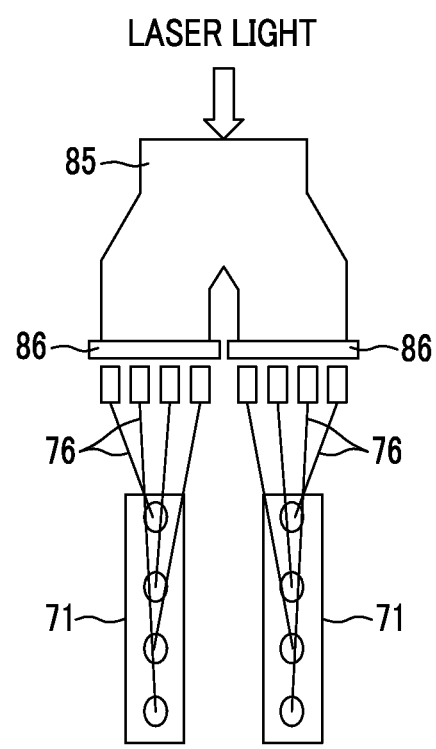
FIG. 12 is a plan view illustrating a portion of the probe according to still another embodiment of the invention.

Next, an embodiment of a structure for improving the quality of the photoacoustic image to be acquired will be described with reference to FIG. 12. A probe shown in FIG. 12 includes a pair of light guides 71 and the light guides 71 have the same basic structure as the above-mentioned light guide 71. Laser light is introduced into the light guides 71 through a plurality of optical fibers 76. The light incident ends of a plurality of optical fibers 76 coupled to one of the light guides 71 form a group and the light incident ends of a plurality of optical fibers 76 coupled to the other light guide 71 form a group. A shutter 86 is provided on the upstream side of each group of the light incident ends of the optical fibers, that is, on the laser light source side. In addition, for example, a shutter including a liquid crystal cell or a mechanical shutter can be used as the shutter 86.

Figure 13:
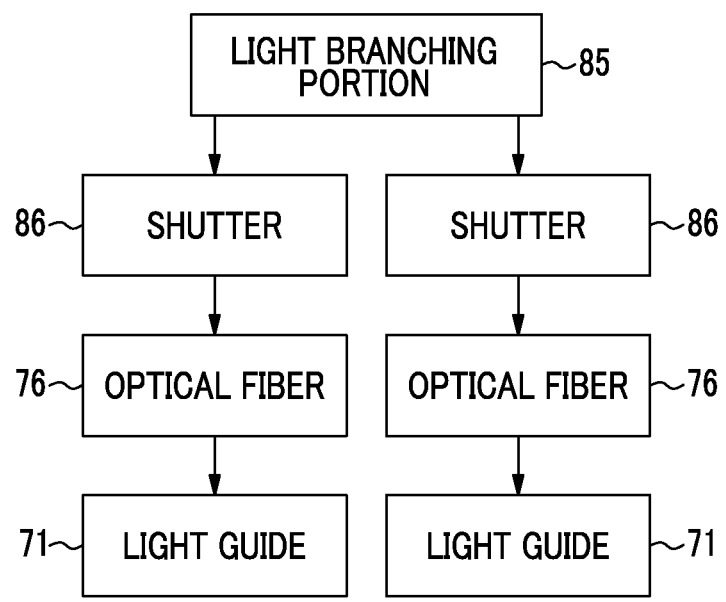
FIG. 13 is a block diagram illustrating the structure of the device shown in FIG. 12.

Laser light which is emitted from a laser light source, such as the laser light source unit 13 passes through a light branching portion 85 which is, for example, a branched light waveguide and is divided into two laser light components. The two branched laser light components are incident on one group of the optical fibers 76 and the other group of the optical fibers 76 through the shutters 86, respectively. FIG. 13 is a block diagram illustrating the above-mentioned structure.

According to this structure, when the image of a given part of the subject is captured, the part is irradiated with laser light which is emitted from the pair of light guides 71. In this case, the opening and closing time of the two shutters 86 is controlled. First, the shutter 86 which is provided on the upstream side of one of the light guides 71 is closed. At that time, the shutter 86 which is provided on the upstream side of the other light guide 71 is opened for a predetermined period of time. When the predetermined period of time has elapsed, the shutter 86 which is provided on the upstream side of the one light guide 71 is opened for a predetermined period of time. At that time, the shutter 86 which is provided on the upstream side of the other light guide 71 is closed. The same operation is repeated and the part is sequentially selectively irradiated with light emitted from the two light guides 71 in two different directions.

When the part to be imaged is irradiated with light in two different directions, the photoacoustic data is acquired in each light irradiation direction in synchronization with the opening and closing time of the two shutters 86. When a photoacoustic image is constructed, two data items for the same pixel in each light irradiation direction are added and averaged and data for the pixel is obtained. According to this process, the S/N ratio of the constructed image is theoretically two times more than that in the usual case. In addition, it is possible to suppress an artifact signal which is generated in a part other than the part immediately below the ultrasonic oscillator 72 (see FIG. 1), that is, a part other than the part that is irradiated with light in two different directions.

Figure 14:
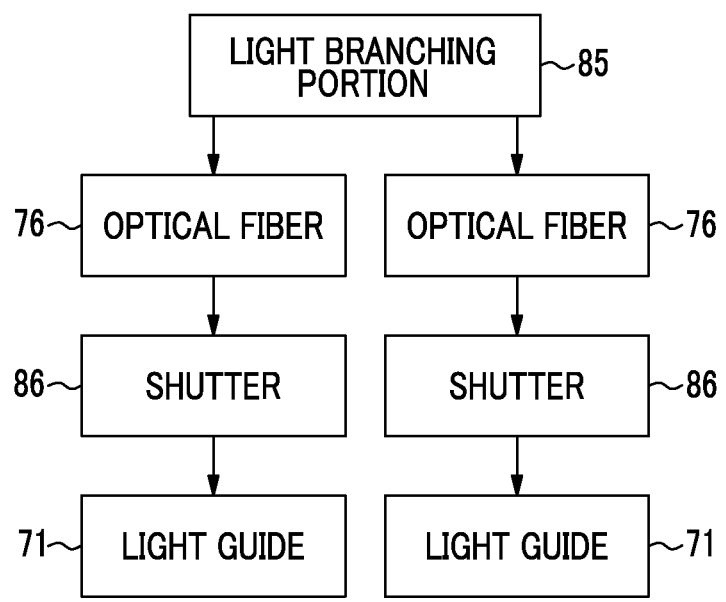
FIG. 14 is a block diagram illustrating a modification of the device shown in FIG. 12.
Figure 15:
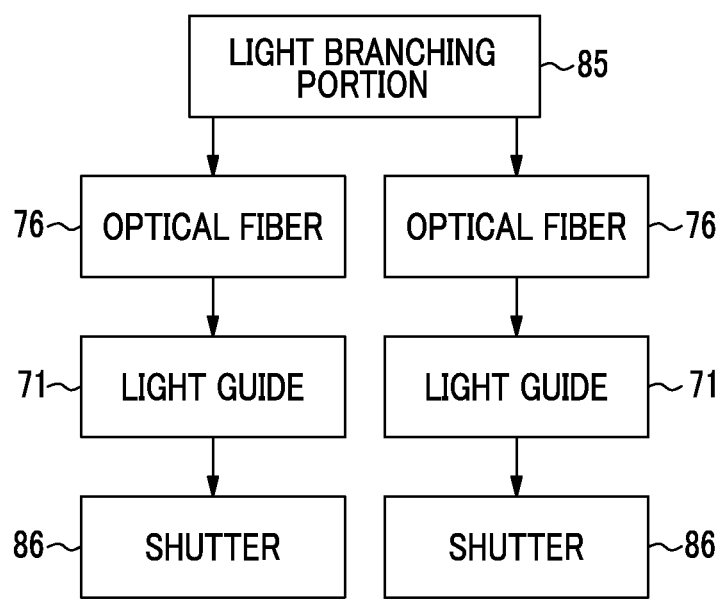
FIG. 15 is a block diagram illustrating another modification of the device shown in FIG. 12.

In this example, the shutter 86 is arranged on the upstream side of the optical fiber 76. However, the invention is not limited thereto. For example, the shutter 86 may be arranged between the optical fiber 76 and the light guide 71, as shown in the block diagram of FIG. 14. In addition, the shutter 86 may be arranged on the downstream side of the light guide 71, as shown in FIG. 15.

Figure 16:
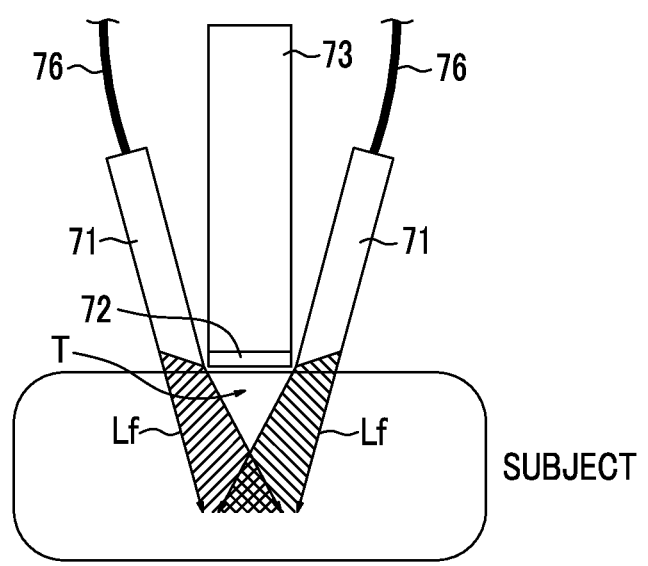
FIG. 16 is a schematic diagram illustrating light radiation from the probe according to the invention.

Next, an embodiment of a structure which can capture high quality images from both a relatively shallow part and a deep part of the subject will be described with reference to FIGS. 16 to 22. When the light guides 71 are obliquely arranged as shown in FIG. 16 and the irradiation state of laser light Lf emitted from the light guides 71 is represented by a hatched portion, a region of a relatively shallow part (a part represented by T in FIG. 16) immediately below the ultrasonic oscillator 72 is not irradiated with light. Therefore, it is difficult to acquire a photoacoustic image signal from a part of the subject in the vicinity of the surface of the subject. In contrast, it is possible to acquire a good photoacoustic image signal from a deep part of the subject.

In addition, when the light guide 71 is vertically arranged, that is, when the light guide 71 is arranged so as to be parallel to the probe axis C and to vertically face the surface of the subject, a large amount of light is absorbed in the vicinity of the surface and only a weak photoacoustic image signal is generally acquired from a deep part of the subject. In contrast, a good photoacoustic image signal can be acquired from a part of the subject in the vicinity of the surface of the subject.

In this embodiment, in order to correspond to the above, the light guide 71 can be switched between an obliquely arranged state and a vertically arranged state. That is, in this embodiment, it is possible to arbitrarily set the probe to a state in which a probe housing 90 is elongated in the arrangement direction of a pair of light guides 71 and the light guides 71 are obliquely arranged as shown in the side view of FIG. 17 and the plan view of FIG. 18 and a state in which the probe housing 90 is shortened in the direction and the light guides 71 are vertically arranged as shown in the side view of FIG. 19 and the plan view of FIG. 20.

Figure 18:
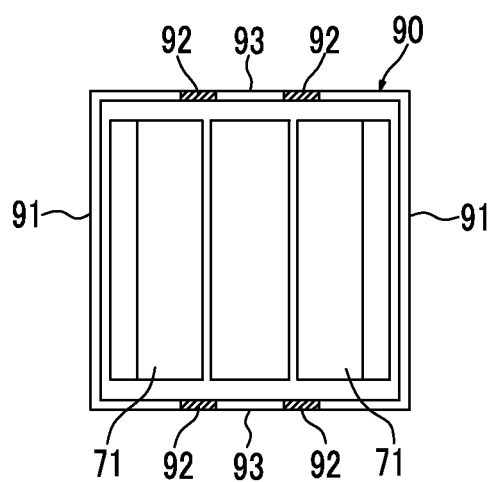
FIG. 18 is a plan view illustrating the planar shape of the probe shown in FIG. 17.
Figure 20:
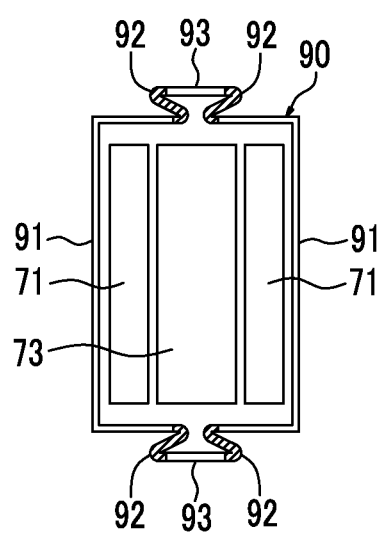
FIG. 20 is a plan view illustrating another state of the probe shown in FIG. 17.

As shown in FIGS. 18 and 20 in detail, the probe housing 90 includes a pair of side end portions 91 that have a U shape in a cross-sectional view, flexible portions 92 that are connected to the ends of bent portions of the side end portions 91, and a central portion 93 that connects the flexible portions 92. The flexible portion 92 can be made of, for example, a rubber material.

In this structure, as shown in FIG. 18, the bent portion of the side end portion 91, the flexible portion 92, and the central portion 93 extend in a line and it is possible to increase the size of the probe housing 90 in the direction in which the light guides are arranged. In this state, the light guides 71 can be obliquely arranged. When the image of a deep part of the subject is captured, it is preferable to capture the image in this state.

As shown in FIG. 20, the pair of side end portions 91 are close to each other and the flexible portions 92 are bent such that the central portion 93 is disposed outside the bent portions of the side end portion 91. In this way, it is possible to reduce the size of the probe housing. In this state, the light guides 71 are vertically arranged and the size of the probe is reduced. When the image of a part of the subject in the vicinity of the surface is captured, it is preferable to capture the image in this state.

Figure 17:
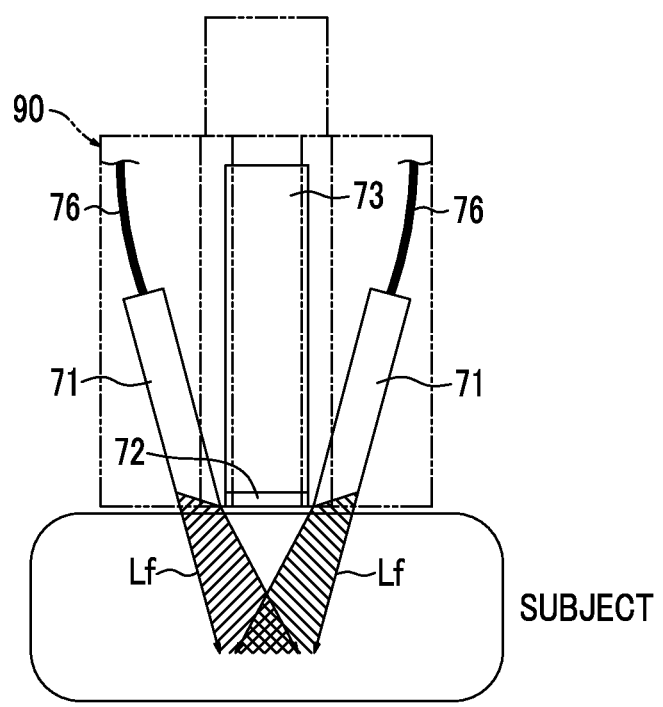
FIG. 17 is a side view illustrating a portion of a probe according to another embodiment of the invention.
Figure 19:
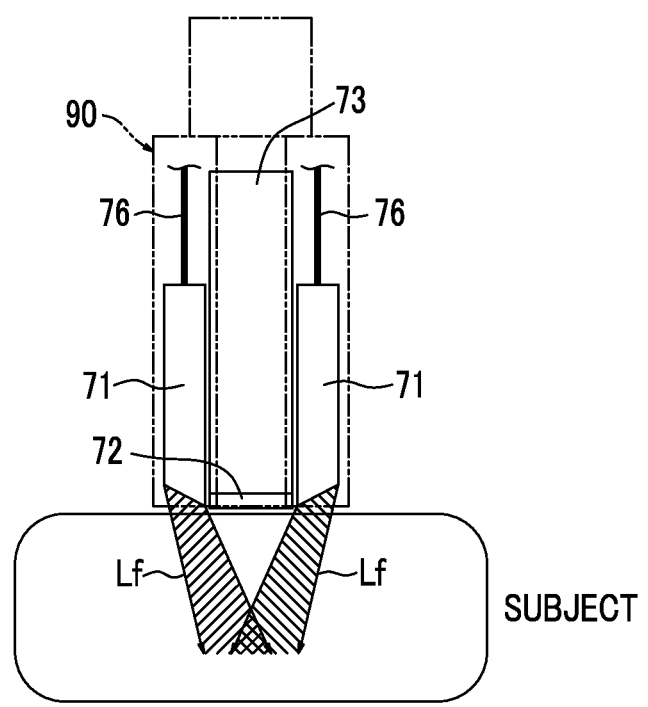
FIG. 19 is a side view illustrating another state of the probe shown in FIG. 17.

It is desirable that the photoacoustic image obtained in the state shown in FIG. 17 be composed with the photoacoustic image obtained in the state shown in FIG. 19 to form an image of the subject including a part in the vicinity of the surface to a deep part. The composite image has a high diagnosis performance. A detailed numerical example will be described. It is preferable that the image of a region from the surface of the subject to a depth of about 5 mm be captured in the state shown in FIGS. 19 and 20 and the image of a region deeper than the above-mentioned region be captured in the state shown in FIGS. 17 and 18.

Figure 21:
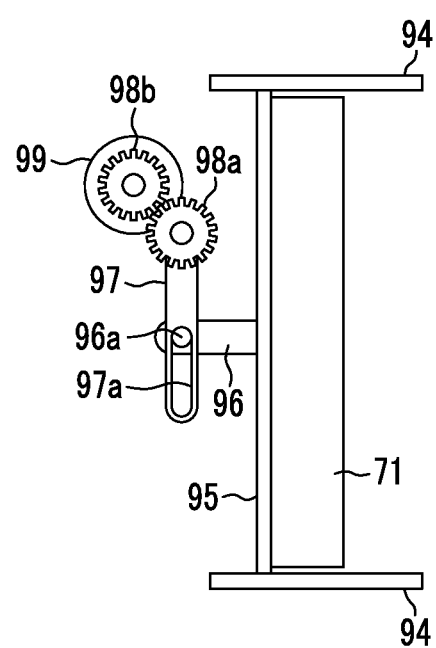
FIG. 21 is a plan view illustrating an example of a mechanism which changes the arrangement angle of a light guide.
Figure 22:
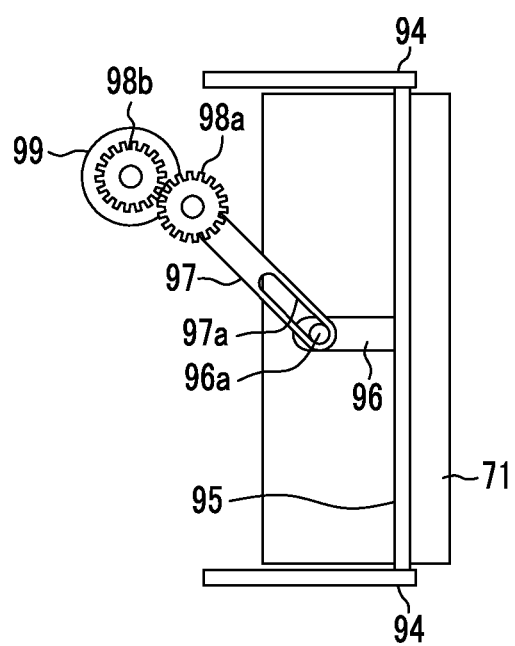
FIG. 22 is a plan view illustrating another state of the mechanism shown in FIG. 21.

An example of a mechanism for changing the arrangement angle of the light guides 71 will be described with reference to FIGS. 21 and 22. FIGS. 21 and 22 show the planar shape of the mechanism when the light guide 71 is vertical arranged and when the light guide 71 is obliquely arranged, respectively. As shown in FIGS. 21 and 22, the mechanism includes a pair of guide rails 94, a light guide retainer 95 which has ends connected to the guide rails 94 and is movable in the left-right direction of FIGS. 21 and 22, a pin fixing portion 96 which includes a pin 96*a* extending in a direction perpendicular to the plane of FIGS. 21 and 22 and is fixed to the light guide retainer 95, an arm 97 including a long hole 97*a* which is fitted to the pin 96*a*, a first spur gear 98*a* which is fixed to the arm 97, a second spur gear 98*b* which is engaged with the first spur gear 98*a*, and a motor 99 which rotates the second spur gear 98*b*.

The light guide 71 can be pivoted between the obliquely arranged position shown in FIG. 17 and the vertically arranged position shown in FIG. 19 and is held by a light guide holding member (not shown). A portion of the light guide 71 which is close to the upper end is connected to the light guide retainer 95 by connection means (not shown).

In the state shown in FIG. 21, the light guide retainer 95 are set at the left end position in FIG. 21 and the light guide 71 connected to the light guide retainer 95 is vertically arranged. In this state, when the motor 99 is driven to rotate the second spur gear 98*b* by a predetermined rotation angle in the clockwise direction, the first spur gear 98*a* is rotated in the counterclockwise direction and the pin fixing portion 96, that is, the light guide retainer 95 is pressed to the right side in FIG. 21 by the arm 97. Then, when the light guide retainer 95 is moved to the right in FIG. 21 by a distance corresponding to a predetermined rotation angle of the second spur gear 98*b*, it is in the state shown in FIG. 22. When the light guide retainer 95 is moved to this position, the upper end of the light guide 71 connected to the light guide retainer 95 is moved and the light guide 71 is in the obliquely arranged state shown in FIG. 17.

In this state, when the motor 99 is driven in a direction opposite to the above-mentioned direction to rotate the second spur gear 98*b* by a predetermined rotation angle in the counterclockwise direction, the first spur gear 98*a* is rotated in the clockwise direction and the pin fixing portion 96, that is, the light guide retainer 95 is drawn to the left side of FIG. 22 by the arm 97 and the light guide 71 returns to the state shown in FIG. 21, that is, the vertically arranged state.

Here, the oblique arrangement angle of the light guide 71 is set to one value. However, the oblique arrangement angle may be set to two or more values.

Next, an example of a structure for holding a state in which a plurality of optical fibers 76 and the light guides 71 are optically coupled to each other will be described with reference to FIG. 23. A holding structure shown in FIG. 23 includes a pair of light guide fixing members 60 which are arranged with the base portion 73 (see FIG. 1) interposed therebetween, a pair of fiber holding members 61 that have a substantially L shape in a cross-sectional view and are fixed to the light guide fixing members 60 by, for example, screws, and fiber pressing members 62 and 63 which are fixed to the outer surfaces of the fiber holding members 61 by, for example, screws.

Figure 23:
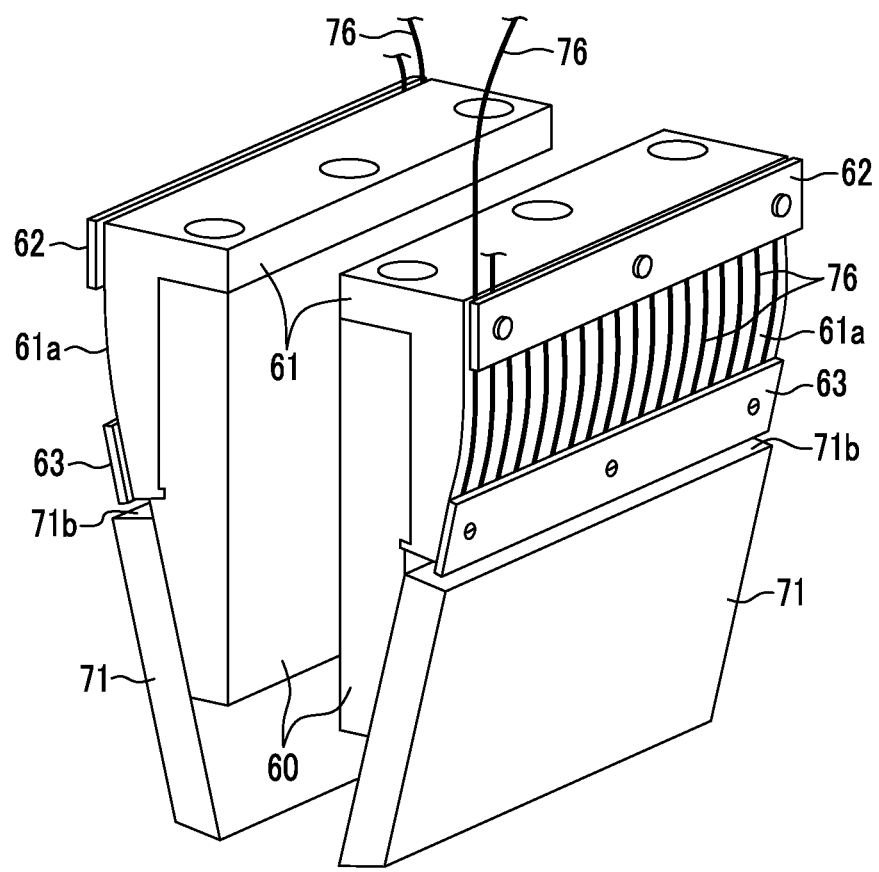
FIG. 23 is a perspective view illustrating an example of a mechanism for holding the light guides and optical fibers.

The light guide 71 is fixed to the light guide fixing member 60 at the position shown in FIG. 23 by, for example, an epoxy-based adhesive. The emission angle of light which is guided by the light guide 71 and is then emitted therefrom depends on the attachment angle of the light guide 71. When the accuracy of the attachment angle is low, the intensity distribution of irradiation light is likely to change. Therefore, in general, there is a demand for fixing the light guide 71 at a predetermined attachment angle with high accuracy. When the light guide 71 is fixed to the light guide fixing member 60 by an adhesive, it is possible to easily meet the demand.

A defect, such as disconnection, is likely to occur in the plurality of optical fibers 76 and an appropriate maintenance operation needs to be performed. Therefore, it is desirable that the plurality of optical fibers 76 be replaced. Portions of the optical fibers 76 which are close to the ends thereof are pressed and fixed to the fiber holding member 61 by the fiber pressing member 63 and portions that are arranged slightly above the portions are pressed and fixed to the fiber holding member 61 by the fiber pressing member 62. For example, each optical fiber 76 is fixed in a state in which the end surface thereof, which is the light emission end surface, faces the light incident end surface 71*b* of the light guide 71 with a very small gap therebetween.

Here, grooves (not shown) for accommodating the optical fibers 76 may be formed in the inner surfaces of the fiber pressing members 62 and 63. In addition, it is desirable that an outer surface 61*a* of the fiber holding member 61 be a gently curved surface such that the optical fibers 76 can be curved and held at, for example, a minimum curvature radius along the curved surface.

According to the fiber holding structure, the fiber pressing members 62 and 63 which are fixed to the fiber holding member 61 by screws can be detached and each optical fiber 76 can be removed for a maintenance operation.

The invention has been described above on the basis of the preferred embodiment. However, the probe for a photoacoustic measurement device according to the invention is not limited only to the embodiment, but various modifications and changes of the structure according to the above-described embodiment are also included in the scope of the invention. The probe for a photoacoustic measurement device according to the invention can be similarly applied to photoacoustic measurement devices other than the above-mentioned photoacoustic imaging device.

What is claimed is:

1. A probe for a photoacoustic measurement device, comprising:
    a light irradiation unit that emits light to be radiated to a subject; and
    an acoustic wave detection unit that detects an acoustic wave which is emitted from the subject by the light irradiation,
    wherein the light irradiation unit includes a light guide that has a parallel plate shape and includes two side surfaces which are parallel to each other, a light incident end surface on which the light is incident, and a light emission end surface which is opposite to the light incident end surface, with the side surfaces interposed therebetween, and from which the light is emitted, the light guide is arranged such that one of the two side surfaces is closer to a probe axis which faces the subject than the other side surface and the light emission end surface is closer to the probe axis than the light incident end surface when the probe is used, and when a refractive index of the light guide with respect to the light is n1 and a refractive index of a medium around the light guide with respect to the light during photoacoustic measurement is n2, an angle α is formed between the light emission end surface and the side surface which is closer to the probe axis, n2<n1 is satisfied, and 90°−arcsin(n2/n1)<α<90° is satisfied.

2. The probe for a photoacoustic measurement device according to claim 1, wherein, when an incident angle of light, which travels in parallel to the two side surfaces in the light guide and is emitted from the light emission end surface, with respect to a plane perpendicular to the probe axis is β1 and an inclination angle of the light guide with respect to the probe axis is β2, the following expression is satisfied:

$$\frac{\sin(90° - \alpha)}{\sin(90° - \alpha + \beta1 - \beta2)} = \frac{n2}{n1} \quad \text{[Expression 1]}$$

3. The probe for a photoacoustic measurement device according to claim 1, wherein an arrangement angle of the light guide is changeable.

4. The probe for a photoacoustic measurement device according to claim 2, wherein an arrangement angle of the light guide is changeable.

5. The probe for a photoacoustic measurement device according to claim 3, wherein the arrangement angle of the light guide is changeable between a predetermined angle with respect to the probe axis and an angle which is parallel to the probe axis.

6. The probe for a photoacoustic measurement device according to claim 4, wherein the arrangement angle of the light guide is changeable between a predetermined angle with respect to the probe axis and an angle which is parallel to the probe axis.

7. The probe for a photoacoustic measurement device according to claim 1, wherein a plurality of the acoustic wave detection units are arranged in a line in a direction perpendicular to the probe axis, and the light guide is arranged such that the light emission end surface extends in the arrangement direction of the plurality of acoustic wave detection units.

8. The probe for a photoacoustic measurement device according to claim 2, wherein a plurality of the acoustic wave detection units are arranged in a line in a direction perpendicular to the probe axis, and the light guide is arranged such that the light emission end surface extends in the arrangement direction of the plurality of acoustic wave detection units.

9. The probe for a photoacoustic measurement device according to claim 3, wherein a plurality of the acoustic wave detection units are arranged in a line in a direction perpendicular to the probe axis, and the light guide is arranged such that the light emission end surface extends in the arrangement direction of the plurality of acoustic wave detection units.

10. The probe for a photoacoustic measurement device according to claim 5, wherein a plurality of the acoustic wave detection units are arranged in a line in a direction perpendicular to the probe axis, and the light guide is arranged such that the light emission end surface extends in the arrangement direction of the plurality of acoustic wave detection units.

11. The probe for a photoacoustic measurement device according to claim 1, wherein two light guides are provided, with the probe axis interposed therebetween.

12. The probe for a photoacoustic measurement device according to claim 2, wherein two light guides are provided, with the probe axis interposed therebetween.

13. The probe for a photoacoustic measurement device according to claim 11, further comprising:

shutters that are provided so as to correspond to the two light guides and control light transmission such that light which passes through the light guides is radiated to the subject for different periods.

14. The probe for a photoacoustic measurement device according to claim 1, further comprising:

optical fibers through which light emitted from a light source is propagated, wherein the optical fibers are optically coupled to the light incident end surface of the light guide.

15. The probe for a photoacoustic measurement device according to claim 14, wherein three or more optical fibers are provided, are arranged in a zigzag pattern in the light incident end surface of the light guide, and are coupled to the light incident end surface.

16. The probe for a photoacoustic measurement device according to claim 14, further comprising:

a light absorber that adheres to a portion of the light incident end surface of the light guide in which the optical fiber is not arranged.

17. The probe for a photoacoustic measurement device according to claim 1, further comprising:

an optical sensor that detects light which is emitted from the light incident end surface of the light guide to the outside of the light guide.

18. The probe for a photoacoustic measurement device according to claim 1, further comprising:

a contact sensor that detects contact of the probe with the subject.

19. The probe for a photoacoustic measurement device according to claim 1, wherein the angle α is in a range of 90°−arcsin(1.33/n1) <α<90°.

20. A photoacoustic measurement device comprising the probe for a photoacoustic measurement device according to claim 1.

* * * * *